Figure 5:
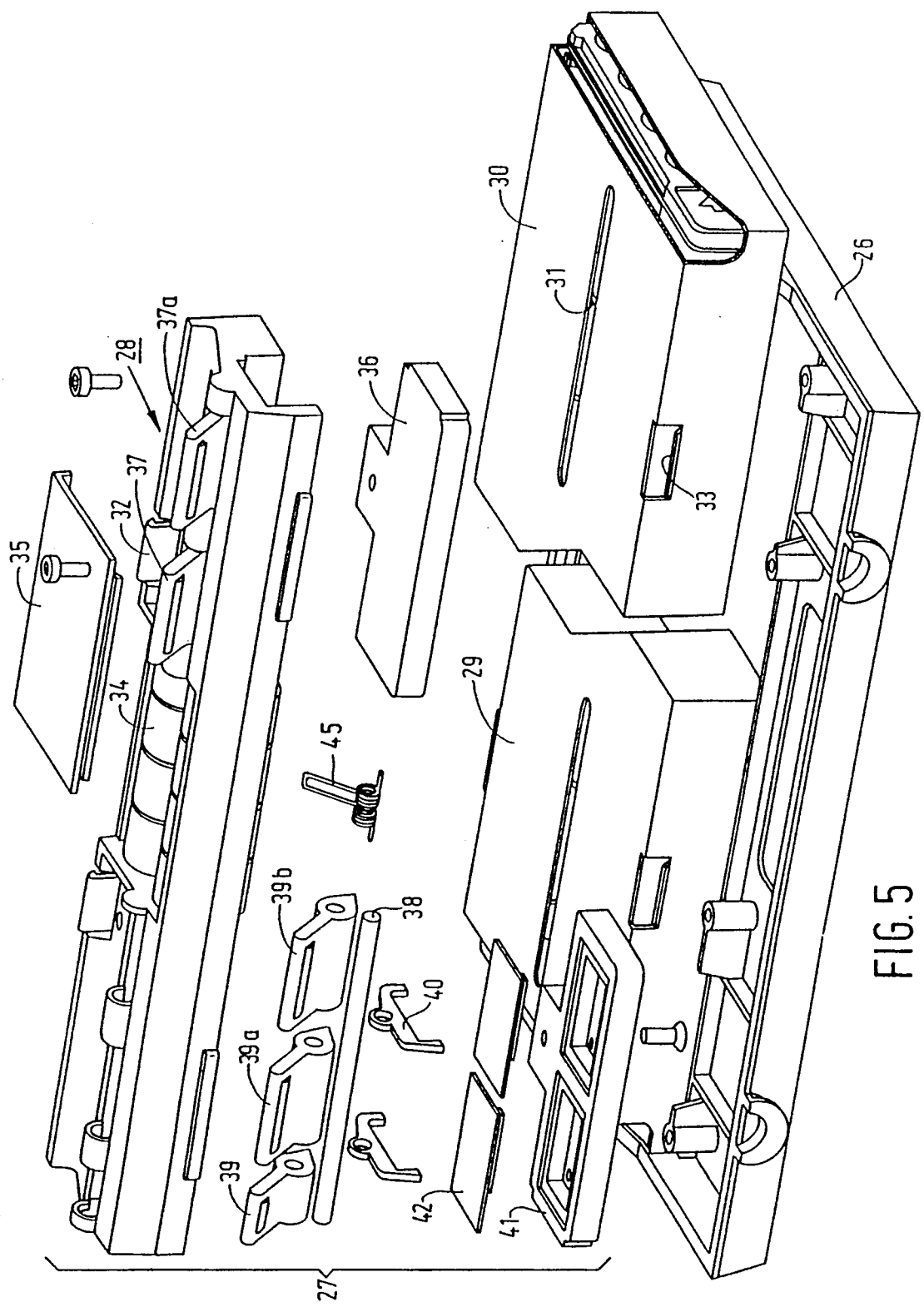

United States Patent [19]

Kleingeld et al.

[11] Patent Number: 5,035,860
[45] Date of Patent: Jul. 30, 1991

[54] DETECTION STRIP FOR DETECTING AND IDENTIFYING CHEMICAL AIR CONTAMINANTS, AND PORTABLE DETECTION KIT COMPRISING SAID STRIPS

[75] Inventors: Adriaan Kleingeld; Kees R. Kooijmans; Wilhelmus F. Kragtwijk, all of Delft, Netherlands

[73] Assignee: Duphar International Research B.V., Weesp, Netherlands

[21] Appl. No.: 481,322

[22] Filed: Feb. 20, 1990

[30] Foreign Application Priority Data

Feb. 24, 1989 [NL] Netherlands ................. 8900459

[51] Int. Cl.$^5$ .................... G01N 31/22; G01N 21/78
[52] U.S. Cl. ......................................... 422/61; 422/58; 422/87; 422/88
[58] Field of Search ............... 422/56, 58, 61, 86–88; 436/165, 167, 104, 902; 435/810

[56] References Cited

U.S. PATENT DOCUMENTS

| | | | |
|---|---|---|---|
| 3,689,224 | 9/1972 | Agnew et al. | 422/61 |
| 3,726,645 | 4/1973 | Kaczmarek | 422/61 |
| 3,740,196 | 6/1973 | Stroterhoff | 422/61 |
| 3,966,412 | 6/1976 | Stroterhoff | 436/165 |
| 4,110,079 | 8/1978 | Schaeffer et al. | 422/56 |
| 4,397,725 | 8/1983 | Enzer et al. | 422/61 |
| 4,978,502 | 12/1990 | Dole et al. | 435/810 |

*Primary Examiner*—Robert J. Warden
*Assistant Examiner*—Howard Hampel
*Attorney, Agent, or Firm*—Stevens, Davis, Miller & Mosher

[57] ABSTRACT

The invention relates to a portable detection kit including a number of detection strips and at least one device for breaking reservoirs within the detection strips. The detection strips detect and identify chemical air contaminants and comprise a holder. The holder has a plurality of spaced carriers which are capable of absorbing the air contaminants and optionally comprise reagents which can be influenced by the air contaminants. The holder further has a plurality of color-producing agents opposite to the carriers. The agents, in contact with the absorbed air contaminants or with the reagents, can cause a color reaction in the presence of a liquid. The color-producing agents, which are dissolved in the quantities of liquid required for the color reaction, are held in closed reservoirs having easily breakable walls. The collective reservoirs are provided between the carriers and a flexible strip is such a manner that when mechanical pressure is exerted on the flexible strip at the area of the reservoirs, the flexible strip will yield, as a result of which the reservoirs will break and the contents thereof will be contacted with the absorbed air contaminants or with the reagents.

5 Claims, 2 Drawing Sheets

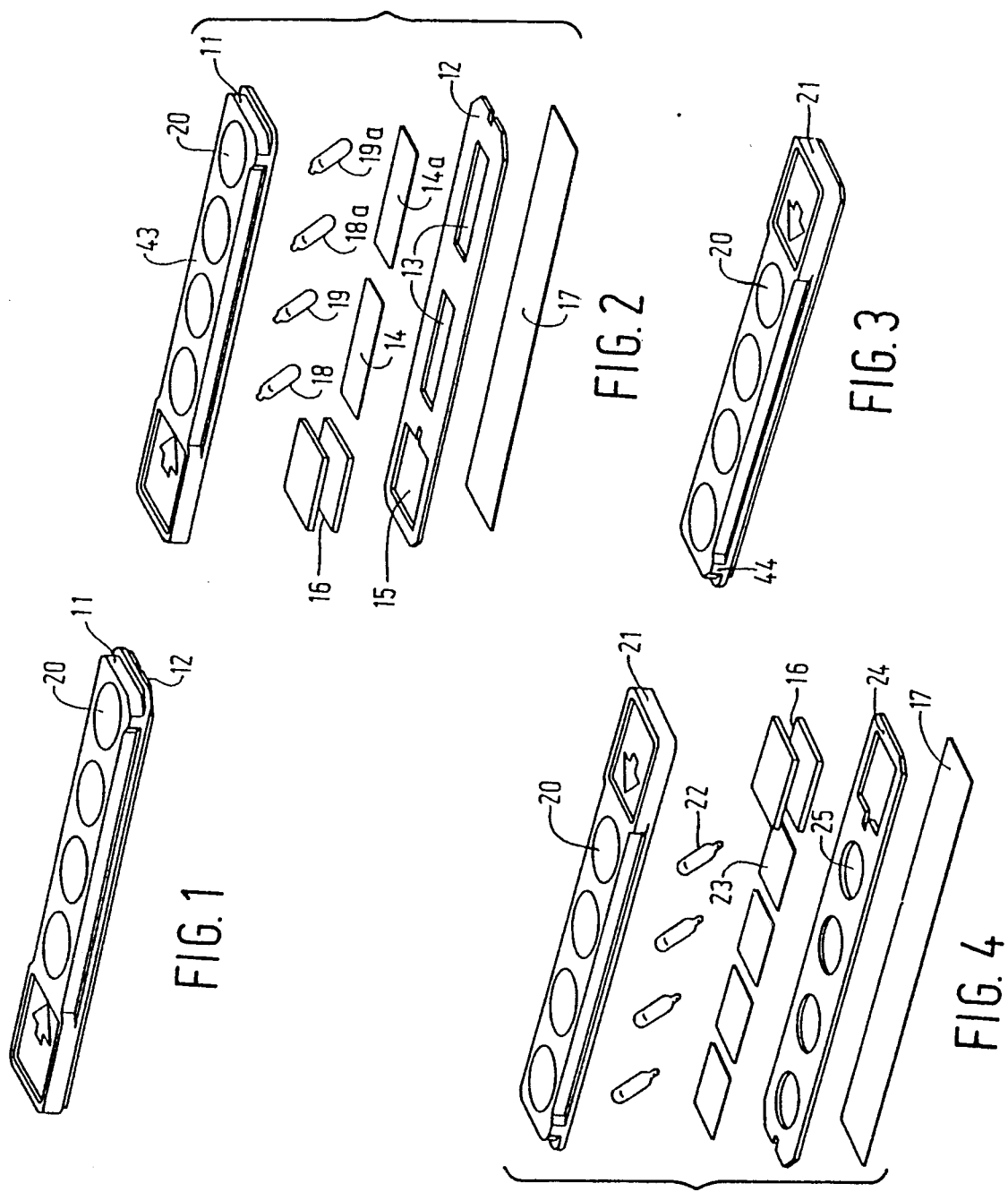

DETECTION STRIP FOR DETECTING AND IDENTIFYING CHEMICAL AIR CONTAMINANTS, AND PORTABLE DETECTION KIT COMPRISING SAID STRIPS

The invention relates to a detection strip for detecting and identifying chemical air contaminants. The strip comprises a holder having a plurality of spaced carriers, which are capable of absorbing the air contaminants and which optionally comprise reagents which can be influenced by the air contaminants, and having a plurality of color-producing agents oppositely to the carriers, which agents, in contact with the absorbed air contaminants or with the reagents, depending on whether or not said reagents have been influenced, can cause a color reaction in the presence of a liquid.

Such a detection strip is known from British Patent Specification 1,277,193. After exposure to the air to be detected, the detection strip disclosed herein is foled on the provided folding line, such that the color-producing agents and carriers with reagents are then facing each other. The carriers have meanwhile been wetted by a liquid from manually ruptured containers. By subsequently manually pressing the color producing agents and the carrier firmly in contact with each other, color reactions can be produced. Color changes can be observed through the transparent carriers. In principle, various different air contaminants can be detected simultaneously independently of each other. This is not the case with the detector described in Euorpean Patent Specification 35,311. This detector, however, can be manipulated simply by exerting pressure on the holder. The carrier with reagent and color producing agent are then contacted with each other, while a liquid container is simultaneously being rupture by piercing. As a consequence the carrier is wetted with the reagent and the color reaction can take place.

A dsadvantage of the strip known from Bristish Patent Specification 1,277,193 is that various manipulations have to be carried out to produce the color reaction. Of course, such a laborious process is time-consuming. Especially since detection strips usually have to be used in emergency situations, namely to enable the detection of warfare gases in wartime conditions. In such circumstances the user is also hindered by the gas-protecting clothing which he is wearing, for example, a gas mask and protective gloves. In addition, the known detective strip is so complicated that the correct use is not possible without elaborate instructions. As a result of this complicated design, it is difficult to manufacture the strip in large quantities at an acceptable, economical price. Finally, manually operated devices are always less reliable than mechanically operated devices. Therefore, the use of mechanically operated devices is preferred.

It is the object of the present invention to provide a detection strip of the type mentioned above with which a plurality of different air contaminants can simultaneously be detected individually and which does not exhibit the above disadvantages.

This object can be achieved by a detection strip for detecting and identifying chemical air contaminants, which is characterized in that the color-producing agents, dissolved in the quantities of liquid required for the color reaction, are contained in closed reservoirs having an easily breakable wall. The collective reservoirs are provided between the carriers and a strip of a slightly flexible material (flexible strip) in such a manner that when a mechanical pressure is exerted on said flexible strip at the area of the reservoirs, said flexible strip will yield, as a result of which the reservoirs, when the carriers are supported, will break and the contents thereof will be contacted with the absorbed air contaminants or with the reagents.

The detection strip according to the present invention may very simply be used by placing the strip in a device suitable for that purpose and by breaking the reservoirs, with mechanical pressure, said reservoirs containing in addition to the quantities of liquid required for the color reaction, the color-producing agents. After having taken the detection strip out of the device it may be exposed to the air to be examined, air contaminants to be detected being absorbed by the carriers. Color reactions may take place by the contact of the contents of the reservoirs with the absorbed air contaminants or with the reagents which may or may not be influenced by the air contaminants. If desired, the strip, after having been exposed to the air, may be replaced in the device to undergo another necessary or desirable treatment, for example, heating and/or adding an auxiliary substance and/or solvent. Color formation or color change can easily be observed visually in the detection strip according to the invention, for example, through inspection windows which are recessed in the bottom of the holder and which correspond to the carriers.

The carriers are manufactured from an absorbing material, for example from a filtering paper of a suitable quality. The reagents optionally used are adapted to the chemical air contaminants to be expected. Various enzymes are sensitve to cerain poisonous substances which may contaminate the air, such as pesticidal compounds and warface gases which may be used in chemical warfare. Examples of enzymes to be used as reagents are cholinesterase and cholinesterase compounds, for example, butyryl cholinesterase. The color-producing substance and liquid in turn are adapted to the air contaminant to be expected, or the reagent to be used. When the above enzymes are used as reagents, for example, 2,6-dichloroindophenyl acetate or a mixture of α-naphthyl acetate and diazonium blue are suitable color-producing substances. The color reaction often takes place under the influence of two color-producing substances or one color-producing substance and an auxiliary substance or solvent, in which the various substances are not compatible for a long period of time or first one and then the other substance has to come available for the color reaction. As will become apparent from the drawings attached which explain the invention, the detection strip according to the invention is also extremely suitable to contain therein two (or even more) reservoirs, the contents of which, together with the absorbed air contaminant to be detached or with reagent, cause the color reaction. When such a detection strip in used, the two reservoirs are then, for example, successively broken, upon which the contents are released and can contact the air contaminant or reagent on the carrier. The quantities of color-producing agent and liquid required for the color reaction may be very small; one drop or a few drops of the solutionn of the color-producing agent in a suitable solvent will usually suffice. An example of a suitable reservoir for such a solution is a so-called sachet of a suitable material which on the one hand is compatible with the solution of the color-producing agent but on the other hand can easily be "broken", i.e. ruptured. Such a sachet may be ruptured, for example, by providing a number of piercing pins in the holder which are capable of breaking the sachet wall, as described in the European Patent Specification 35,311 mentioned above. However, it has proved advantageous to manufacture such a reservoir from glass. The solution of the color-producing agent is provided in glass ampoule which is hermetically sealed and optically under oxygen-free conditions, since glass is inert with respect to the ingredients of the solution. Moreover, glass ampoules have proved to be excellently suitable for the storage of particularly small quantities of liquid for a long period of time without the stability thereof being detrimentally influenced.

In a favorable embodiment the detection strip according to the invention comprises a holder which has a base or bottom plate in which inspection windows are recessed. The carriers, for example, sheets of filtering paper which may comprise reagents, are provided on said inspection windows. The filled and sealed ampoules, as explained above, are situated above said carriers, while the holder is closed on its upper side by a strip which is flexible at the area of the ampoules and is manufactured from a suitable material, for example a slightly resilient synthetic material. To be able to store the contents of the detection strip, in particular the carriers optionally provided with reagents, in a hermetically sealed and dry manner before usng the strip, the detection strip in this embodiment comprises on its lower side a sheet of an impervious material with which the inspection windows in the lower plate are covered, and the strip comprises a drying agent. Optionally, the holder comprises on its lower side, beside or around the inspection windows, a color impression with which the color observed through the inspection windows can be compared and the visual evalution can thus be facilitated.

The invention also relates to a portable detection kit for detecting and identifying chemical air contaminants. Such a detection kit according to the invention comprises a number of detection strips as defined above and at least one device for breaking the reservoirs contained in the detection strips. The strips may be contained in the detection kit, for example in one or more cassettes. A device for breaking the reservoirs comprises one or more spaced switches, a base plate and an open space between switches and base plate which is proportioned to that a detection strip can be inserted into it, in which the switches can be moved, optionally against spring action, and are constructed so that in the presence of a detection strip provided in the device, upon switching, a mechancial pressure is exerted on the reservoirs via the slightly flexible strip, said pressure causing the reservoirs on the carriers supported by the base plate to be broken.

When the switches are moved from the quiescent state into the operative state, the reservoirs of the detection strip present in the device will break. The detection strip may now be taken out of the device and may be inspected after having been exposed to the air to be examined. In the presence of spring means, the switches will return to their quiescent state under the influence of the spring force, so that it will then be clear to the user that the device is ready to receive a fresh detection strip. The switches may be constructed as push-button switches, rotary switches, tumbler switches, and the like. The springs may be adapted to the type of switches used; for example, compression springs may be used for push-buttom switches and torsion springs may be used for tumbler switches. The switches should, of course, comprise finger grips which enable ease of operation, even with the gloved hand. The detection strips must be inserted in the correct position into the device for breaking the reservoirs. Therefore, the detection strips preferably comprise an indication, for example, in the form of a clearly visible arrow, which is provided on the top side of the strip and which indicates how the strip is to be inserted into the device. In order to avoid any mistakes, the strip may additionally comprise a provision which prevents the strip either from being inserted in the wrong direction into the device or from being inserted into a device differing from that for which the strip is intended.

According to another aspect of the present invention, the detection kit is also suitable for detection strips which comprise ingredients which produce a color reaction with the absorbed air contaminants, or the influenced reagents, only at elevated temperature. For that purpose, the base plate of the device for breaking the reservoirs provided in the detection strips may comprise one or more thermostatic heating elements. After switching on said heating elements, the base plate is kept at the temperature desired for the color reaction in that place or those places which correspond to the ingredients provided in the detection strip and required for this color reaction, in case the strip has been inserted into the device. All this will be described in greater detail below with reference to the accompanying drawings.

As stated above it is advantageous that the reservoirs comprising the color-producing agent and the liquid required for the color reaction are manufactured from glass. In a preferred embodiment the device for breaking said glass ampoules comprises one or more switches which are constructed as tilting cams which can be pivoted around a pin and can be switched against spring action, and which, when switching from the quiescent state into the operative state, cause the glass reservoirs to be broken. When switching such a tumbler switch from the quiescent state into the operative state, the cam of the switch will exert a mechanical pressure on the flexible strip which is present on the top side of the detection strip and which is slightly flexible at the area of the ampoules, as a result of which the ampoules or ampoules provided between said strip and the carrier or carriers supported by the base plate breaks or break. It is further of advantageous to construct the device for breaking the ampoules in the detection strip in such a manner that the user has a clear visual indication that the device has been used, i.e. that the ampoules in the strip have been broken. In behalf of such a visual indication of "having been used", the tilting cams are preferably constructed so that after switching to the operative state they are blocked by the presence of the detection strip provided in the device and that they can return to their quiescent state under the influence of the spring action only after the removal of the detection strip. In this preferred embodiment the dimensions of the detection strip, of the open space between tilting cams and base plate of the device, and of the tilting cams themselves are matched to each other in such a manner that the spring action is not sufficient to push the tilting cams over the detection strip back to their quiescent state; the tilting cams return only after the removal of the detection strip.

In addition to the detection strips which are contained, for example, in one or more cassettes, the device or devices for breaking the reservoirs in the detection strips and optionally the heating elements, the detection kit according to the invention may also provide space for other utensils for detecting air contaminants. For example, the detecting kit according to the invention may comprise reporting material in the form of notebooks and writing materails, detection stickers, pouches and the like for taking, samples of soil, leaves, and the like, as well as directions for use. The detection kit may further comprise sampling tubes, in particular passive sampling tubes, as described in the non-prepublished Netherlands Patent Applications No. 8801682. The detection kit will be constructed, for example, as a suitcase in which all the ingredients required for the detection are contained and which may comprise a handle and/or means for attachement to a belt or sling. Certain treatments require certain periods of time. For completion of the instructions the detection kit may comprise an electronic time warning system which after each operation indicates to the user that an operation has been completed by means of an optical or acoustical signal.

The invention will now be described in greater detail with reference to the drawings, in which:

FIGS. 1 and 3 are perspective views of two different detection strips according to the invention, FIGS. 2 and 4 show the same detection strips in an exploded view, and FIG. 5 is a perspective view, partly broken away, of a detection kit according to the invention.

In the detection strips shown in FIGS. 1-4, the direction in which the strips are to be inserted into the devices for breaking the reservoirs is indicated by means of arrows. The strip shown in FIGS. 1 and 2 comprises a holder 11 having a separate base plate 12 which is connected to the holder and in which two inspection windows 13 are recessed. Two carriers (sheets of filtering paper) 14 and 14a, which may optionally be provided with different reagents and which in the assembled conditions of the strip cover the windows, bear on said base plate. The base plate further comprises a recess 15 for a drying agent, for example a silica-gel-impregnated paper or textile. On its lower side the strip is sealed by means of a sheet 17 of a suitable material. Sealed ampoules comprising solutions of color-producing agents, liquids and/or auxiliary substances: 18-18a, 19-19a, are situtated above the carriers. As will be obvious from FIG. 2, the contents of ampoule 18 together with those of ampoule 19 may cause a color reaction on carrier 14, of course, after having been exposed to the air, while the contents of ampoule 18a together with those of ampoule 19a can also cause a color reaction, in this case on carrier 14a. On its upper side, the holder comprise a strip 43 having circular, thin and hence flexible areas 20 which correspond to the ampoules.

The detection strip shown in FIGS. 3 and 4 corresponds in outline to that shown in FIGS. 1 and 2. On its upper side, the holder 21 again comprises a strip having flexible area 20 which correspond to four sealed ampoules 22. Each ampoule comprises a solution of a color-producing agent, which may cause a color reaction on a carrier 23 (sheet of filtering paper) after having been exposed to the air. Consequently there are four carriers which correspond to the ampoules and which bear on base plate 24 having four inspection windows 25 recessed therein. The detection strip shown in FIGS. 3 and 4 further comprises a drying agent 16 and a covering sheet 17. The detection strip finally comprises a cam 44 which prevents the improper use of the strip. The use of the detection strips will be described in greater detail with reference to the detection kit shown in FIG. 5.

The detection kit shown in FIG. 5 comprises two devices 27 and 28 for breaking the ampoules in the detection strips, said devices being mounted on the bottom 26 of a suitcase, the cover of which is hingeably connected to the bottom and is not shown. The cover further comprises fastening eyelets for a set of a carrying straps and, of course, means for attachment to the bottom. The detection kit further comprises two so-called "easy-refill" cassettes 29 and 30 comprising fresh, i.e. unused detection strips, cassette 29 comprising detection strips of th type shown in FIGS. 1 and 2 and cassette 30 comprising detection strips of the type shown in FIGS. 3 and 4. The cassettes which internally comprise leaf springs (for example 31) are connected to the devices 27 and 28 by means of resilient catches (for example 32-33). The devices 27 and 28 for breaking the ampoules are mounted on the bottom 26 of the suitcase by means of screw-bolts, and are connected together via a holder comprising batteries 34 and a cover plate 35 and thus form one assembly. Drive 28 is shown in the assembled condition - the base plate 36 excepted - and comprises two tumbler swiches 37 and 37a. After assembling the base plate, a space remains between the switches and the base plate into which a detection strip as shown in FIGS. 3 and 4 can be inserted. The device 27 shown in exploded view comprises three tumbler switches in the form of tilting cams 39, 39a and 39b which can pivot around a pin 38 and which can be moved from the quiescent state into the operative state against the action of double-torsion springs (one spring 45 is shown). The base plate 41 fixes the supports 40 destined for the pivot pin in the device 27. The base plate comprises two thermostatic heating elements 42. Each heating element has its own constant temperature which is obtained by the use of temperature-dependent resistors. Independent of the ambient temperature, the desired temperature for the color reaction can be obtained by means of these heating elements. The heating is switched on by means of one of the switches. Device 27 serves for breaking the ampoules in the detection strip shown in FIGS. 1 and 2, in which the color reactions have to take place at elevated temperatures. When using the detection kit, the detection strip shown in FIGS. 3 and 4, after removing sheet 17, is inserted into the device 28, the cam 44 provided on the strip ensuring the correct insertion of the strip. This cam also prevents the strip from being inserted into device 27. When the switch 37 is actuated, the two left-hand ampoules 22 (FIG. 4) are broken; when the switch 37a is actuated the two right-hand ampoules (FIG. 4) are broken. When the strip is taken out of the device, the switches return to their quiescent state. The detection strip is then exposed to the air to be examined, after which the color formation or color change of the carriers 23 can be observed via the inspection windows 25. The detection strip shown in FIGS. 1 and 2 can be inserted into the device 27 in the same manner after sheet 17 has been removed. This strip also comprises a cam to prevent the improper insertion of the strip. After the insertion the switch 39a is acutated, and the ampoules 18a and 19 are broken. The strip is then taken out of the device and exposed to the air. In order to produce the desired color reactions, an elevated temperature is required and the ingredients contained in the ampoules 18 and 19a are also necessary. Therefore after exposure to the air to be examined, the strip is re-inserted into the device 27. By actuating switch 39b ampoule 19a is broken and the heating of the elements 42 is simultaneously switched on. After some time switch 39 is actuated, breaking ampoules 18. When the detection strip is taken out of the device a color change of the carriers 14 and 14a, if any, can be observed via the inspection window 13.

In addition to the detection kit shown, the suitcase 10 may comprise useful auxiliary means for detecting contaminants are described above.

What is claimed is:

1. A portable detection kit for detecting and identifying chemical air contaminants, comprising a number of detection strips and at least one device for breaking the reservoirs contained in the detection strips, said device comprising one or more spaced switches, a base plate and an open space between the switches and the base plate which is proportioned so that a detection strip can be inserted into it, in which the switches can be switched, and are constructed so that in the presence of a detection strip provided in the device, upon switching a mechanical pressure is exerted on the reservoirs via a flexible strip, said pressure causing the reservoirs on the carriers supported by the base plate to be broken, wherein the detection strips each comprise a holder having a plurality of spaced carriers, which are capable of absorbing the air contaminants and having a plurality of color-producing agents opposite the carriers, which agents, in contact with the absorbed air contaminants, can cause a color reaction in the presence of a liquid, said detection strip being characterized in that the color-producing agents, dissolved in the quantities of liquid required for the color reaction, are contained in closed reservoirs having walls which are easily broken by mechanical force, and the collective reservoirs are provided between the carriers and a flexible strip in such a manner that when a mechanical pressure is exerted on said flexible strip at the area of the reservoirs said flexible strip will yield, as a result of which the reservoirs, which are supported by a suitable support, will break and the contents thereof will be contacted with the absorbed air contaminants.

2. A detection kit as claimed in claim 1, wherein the base plate of the device for breaking the reservoirs provided in the detection strips comprises one or more thermostatic heating elements.

3. A detecttion kit as claimed in claim 1 or 2, wherein the reservoirs are manufactured from glass and the switches are constructed as tilting cams which can be pivoted around a pin, said cams causing the glass reservoirs to be broken when the switches are moved from a quiescent state into an operative state.

4. A detection kit as claimed in claim 3, wherein the tilting cams are constructed so that, after switching to the operative state, they are blocked by the presence of a detection strip provided in the device and that they can return to their quiescent state only after removing the detection strip.

5. A detection kit as claimed in claim 1, wherein the spaced carriers further comprise reagents disposed on the spaced carriers which reagents are affected by the air contaminants and exhibit or prevent a color reaction upon exposure to such air contaminants.

* * * * *